United States Patent [19]

Thomas et al.

[11] Patent Number: 5,119,819
[45] Date of Patent: Jun. 9, 1992

[54] METHOD AND APPARATUS FOR NON-INVASIVE MONITORING OF BLOOD GLUCOSE

[75] Inventors: Graham H. Thomas, Livermore; Roger M. Watson, Modesto, both of Calif.; J. Oakey Noell, Mishawaka, Ind.

[73] Assignee: Miles Inc., Elkhart, Ind.

[21] Appl. No.: 517,699

[22] Filed: May 2, 1990

[51] Int. Cl.$^5$ .............................. A61B 8/00; A61B 5/00
[52] U.S. Cl. ................................ 128/660.02; 128/632
[58] Field of Search ............... 128/660.02, 632, 637, 128/597

[56] References Cited

U.S. PATENT DOCUMENTS 4,433,690  2/1984  Green et al. .................. 128/915 X
4,664,124  5/1987  Ingle et al. .................. 128/660.02

Primary Examiner—Francis Jaworski
Attorney, Agent, or Firm—Roger N. Coe; Jerome L. Jeffers

[57] ABSTRACT

A new and improved method and apparatus are provided for non-invasive monitoring of changes in blood glucose concentration in a tissue specimen and particularly in an individual. The method uses acoustic velocity measurements for monitoring the effect of glucose concentration upon the density and adiabatic compressibility of the serum.

In a preferred embodiment, the acoustic velocity measurements are made through the earlobe of a subject by means of an acoustic probe or monitor which includes a transducer for transmitting and receiving ultrasonic energy pulses to and from the blood flowing in the subject's earlobe and a reflector for facilitating reflection of the acoustic pulses from the blood. The probe is designed in such a way that when properly affixed to an ear, the transducer is positioned flush against the anterior portion of an earlobe while the reflector is positioned flush against the interior portion of the earlobe. A microthermocouple is provided on the probe for monitoring the internal temperature of the blood being sampled.

An electrical system, essentially comprising a frequency generator, a time intervalometer and an oscilloscope, is linked to the glucose monitoring probe. The electrical system analyzes selected ones of the pulses reflected from the blood sample in order to determine therefrom the acoustic velocity of the blood which, in turn, provides a representation of the blood glucose concentration levels at the time of the acoustic velocity measurements.

15 Claims, 4 Drawing Sheets

METHOD AND APPARATUS FOR NON-INVASIVE MONITORING OF BLOOD GLUCOSE

BACKGROUND OF THE INVENTION

1. Field of the Invention

The present invention generally relates to a new and improved technique for monitoring changes in blood glucose concentration in a tissue specimen. More particularly, this invention relates to a new and improved method and apparatus for using acoustic velocity measurements as a basis for non-invasive monitoring of blood glucose levels in individuals.

2. Description of the Prior Art

The typical procedure for determining blood glucose concentration in a diabetic or other individual is to secure a blood sample from a finger prick and apply that blood to an enzymatically mediated colorimetric strip or an electrochemical probe. Since a diabetic checking himself for glucose level must perform this procedure several times in a day, it would be desirable if the pain and annoyance of the finger prick and the inconvenience of blood handling could be avoided One obvious way to alleviate this pain and inconvenience is by non-invasive monitoring.

Most non-invasive monitoring techniques have focused on using incident radiation capable of penetrating tissue and probing the blood. Three distinct non-invasive approaches are possible optical, electrical and acoustic. All currently known approaches to non-invasive glucose measurement are either optical or electrical. The optical techniques generally use infrared radiation of a selected wavelength, typically between 890 and 2500 nm, which corresponds to the region of the optical spectrum in which the skin tissue has the highest transmittance. The less successful and relatively uncommon electrical measurements focus upon the dielectric properties of water solutions in a given frequency range, typically between 1-50 MHz. In one form or another, such methods attempt to monitor the influence of glucose or other analyte concentration upon the dielectric frequency response of either the glucose itself or the secondary effect on the water.

Although investigations have been made into the use of acoustic monitoring, past studies have been primarily directed to the differences in acoustic velocity between organs. These studies have attempted to correlate acoustic velocity changes with chronic or continuous disease states. In addition, there is a large body of medical and scientific literature pertaining to the use of acoustic absorptive and scattering properties of organs for imaging, therapeutic and even diagnostic objectives.

The following references provide a background on the use of acoustic velocity measurement for the above purposes: *Ultrasonic Characterization of Blood*, Vol. 2, K. Kirk Shung, Chapter 10; *Ultrasonic Velocity and Attenuation in Mammalian Tissues*, R. C. Chivers, R.J. Parry, Journal of the Acoustical Society of American, March 1978, pp. 940-953; *Tabular Data of the Velocity and Absorption of High Frequency Sound in Mammalian Tissues*, D. E. Goldman, T. F. Hueter, Journal of the Acoustical Society of America, Vol. 28, No. 1, January 1956, pp. 35-37; *Determination of the Acoustical Velocity in Tissues Using an Inhomogeneous Media Model*, David H. Dameron, IEEE Transactions In Sonics and Ultrasonics, Vol. SU-26, No. 2, March 1979, pp. 69-74, *Frequency Decendent Ultrasonic Differentiation of Normal and Diffusely Diseased Liver*, T. Lin, J. Ophir, G. Potter, Journal of the Acoustical Society of America, Vol. 82, October 1987, pp. 11-38; *Ultrasonic Investigation of Solute-Solvent and Solute-Solute Interactions and Aqueous Solutions of Bases, Nucleosides and Nucleotides*, Journal of Physical Chemistry, 1980, pp. 692-696, A. P. Sarvazyan, V. A. Buckin, Paul Hemmes; *Detection of Nocturnal Hypoglycemia In Insulin Treated Diabetics by a Skin Temperature-Skin Conductance Meter*, K. Johansen, S. Ellegaard, S. Wex, Acta Med Scand 1986, pp. 213-217; *Teledyne Sleep Sentry: Evaluation In Pediatric Patients For Detection of Nocturnal Hypoglycemia*. Karla A. Hansen, Stephen C. Duck, Diabetes Care, Vol. 6, No. 6, November-December 1983, pp. 597-600; *An Electrocapillary Flow Meter Useable As a Quantitative Sweat Detector*, Robert Alric, Robert Quatrefages, Jose Comallonga, The American Physiological Society, 1980, pp. 342-346; *Recent Developments in Diagnostic Ultrasound*, K. Kirk Shung, CRC Critical Reviews in Biomedical Engineering, Vol. 15, Issue 1, 1987, pp. 1-25; *Scattering of Ultrasound By Blood*, Ko Ping K. Shung, Rubens A. Sigelmann, John M. Reid, IEEE Transactions on Biomedical Engineering, Vol. BME-23, No. 6, November 1976, pp. 460-467.

SUMMARY OF THE INVENTION

Briefly, the present invention is directed to a new and improved method and apparatus for non-invasive monitoring of changes in blood glucose concentration in a tissue specimen and particularly in an individual. The improved method is based on making an indirect evaluation of the effect of glucose concentration upon a colligative physical property of a fluid More specifically, the method uses acoustic velocity measurements for monitoring the effect of glucose concentration upon specific physical parameters of blood serum, such as the density and adiabatic compressibility of the serum. The acoustic velocity measurements realize accurate measurement of glucose concentration provided that parameter is changing more rapidly than other blood components which affect the acoustic velocity of blood.

According to a preferred embodiment of apparatus for implementing the improved method of this invention, the acoustic measurements are made through the earlobe of a subject by means of an acoustic probe designed to be rigidly affixed onto the subject's ear. The probe includes a transducer for transmitting and receiving ultrasonic acoustic energy pulses and is designed in such a way that when properly affixed to an ear, the transducer is positioned flush against the anterior portion of an earlobe. A reflector is also provided and is mounted on the probe flush against the interior portion of the earlobe.

While ultrasonic pulses are being transmitted and received, the temperature of the tissue specimen is also monitored. This is accomplished by a micro- thermocouple that is enclosed within a cannulae of the probe. The earlobe-mounted probe assembly is electrically connected to a pulse echo monitoring system essentially comprising a frequency generator, a frequency counter, an oscilloscope and a time intervalometer. The transducer is excited to direct a series of acoustic energy pulses at a blood sample. Reflected pulses generated at the front and back surfaces of the sample are captured by the transducer.

A frequency-dependent sinusoidal waveform from the frequency generator causes the intervalometer to create an artificial time delay between the reflected pulses. Adjustments are made to the frequency generator to control this delay in such a way that the two pulses overlap; under these conditions, the travel time between the reflected pulses corresponds to the frequency of the signal used to create the requisite delay. Since the distance between the transducer and the reflector is known, the acoustic velocity can be calculated and changes in the blood glucose concentration determined therefrom.

Many modifications can be made to the monitoring apparatus without substantively altering the intent or function. In one alternative embodiment, for example, the probe carrying the transducer and reflector is adapted to be positioned on opposite sides of the web of skin between the thumb and forefinger of a patient. Other types of probe arrangements can also be made using the concept and intent of the present invention.

BRIEF DESCRIPTION OF THE DRAWINGS

The above advantages and novel features of the present invention will become apparent from the following detailed description of the principle and preferred embodiments of the invention when taken in conjunction with the accompanying drawings wherein.

DESCRIPTION OF THE PREFERRED EMBODIMENT

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Differences in acoustic velocities between different bodily organs have been studied in the past and attempts have even been made to correlate such changes with chronic, as well as continuous, disease states for these organs. There also exists a large body of medical and scientific literature pertaining to the use of the acoustic absorptive and scattering properties of organs toward a variety of objectives including imaging, therapeutic, and diagnostic purposes. Presently available literature and technological details related to the use of acoustic velocity as a monitor of physiological analyte concentrations reveal the absence of teachings directed to the acoustic monitoring of the concentration of specific analytes, in particular glucose, in fluids.

Ultrasonic studies made by the applicants toward measuring the dependence of acoustic velocity on glucose concentration in a serum have demonstrated the presence of a linear relationship between the instantaneous glucose concentration level in the serum and the acoustic velocity of the serum. This relationship is based on the fact that acoustic velocity in a fluid is related to the density and adiabatic compressibility of the fluid in accordance with the following relationship:

$$v = (b/r)^{\frac{1}{2}} \quad (1)$$

wherein "v" is the acoustic velocity (m/s); "b" is the fluid modulus (g/ms$^2$); and "r" is the density (g/m$^3$).

Since changes in the level of glucose concentration in fluids in general, and blood serum in particular, directly affect both the density and adiabatic compressibility of the serum, any changes in glucose concentration also affect the acoustic velocity directly. By employing known principles of ultrasonic measurements, it thus becomes possible to monitor the level of glucose concentration in human blood by making accurate measurements of the acoustic velocity of blood serum.

The improved glucose concentration monitoring technique of this invention is based upon the transmission of pulses of acoustic energy into a sample of blood serum and capturing and analyzing the acoustic energy reflected at both the front surface and the back surface of the sample. Provided that the time of flight for the acoustic energy from the extreme surfaces of the blood sample are accurately measured, and knowing the thickness of the specimen being analyzed, i.e., the distance separating the extreme surfaces, the acoustic velocity of the blood sample can be calculated on the basis of the following relationship.

$$v = 2d/t \quad (2)$$

where "v" represents the acoustic velocity (m/s); "d" represents the distance (m); and "t" represents the time (s).

However, the acoustic velocity in a glucose solution, in this case blood serum, is also strongly dependent on changes in temperature of the solution or the blood sample. Accordingly, for truly representative acoustic velocity measurement, it becomes necessary to develop an analytical model describing the dependence of acoustic velocity on temperature and adjusting the measured velocity accordingly. An analytical model describing the relationship between acoustic velocity and temperature in salt water is given below.

$$v = 1449.2 + 4.6T - 0.055T^2 + 0.00029T^3 + (1.34 - 0.01T)(S - 35) + 0.016P \quad (3)$$

Where "v" is the acoustic velocity in salt water (m/s); "T" is the temperature (°C); "S" is the salinity of the solution (ppm); and "P" is the pressure (atm). This salt water model can either be used directly or preferably modified easily using a small degree of experimental verification in order to generate the requisite temperature relationship for a glucose solution.

In the most elementary form of implementation, the ultrasonic measurements required for monitoring acoustic velocity changes in blood serum and, hence, the corresponding changes in glucose concentration therein, can be based on the conventional time-of-flight technique using a pair of transducers capable of sequentially transmitting and receiving a series of pulses of acoustic energy to and from the blood sample. With this technique, the accuracy of acoustic measurements is restricted and it has been found to be effective only where high glucose concentration levels (up to 8000 mg/dL) exist within the sample.

However, in order to be effective in accurately measuring the variation in blood glucose concentration in humans, it is necessary to accurately measure changes in acoustic velocity corresponding to much lower glucose concentration levels. In fact, in order to be practically effective, it is necessary to measure accurately acoustic velocity changes of one part in 100,000. As an illustration, for the measurement of acoustic velocity in water (where "v" equals 150,000 cm/s), the measurement technique should be capable of detecting changes as small as 1.5 cm/s in acoustic velocity. This required level of accuracy corresponds to more than 10 times that associated with conventional time-of-flight techniques.

In accordance with a feature of this invention, the desired high level of accuracy is achieved by use of a "pulse echo overlap" technique. According to this technique, acoustic velocity measurements are made by using a single transducer which is excited to transmit acoustic energy pulses to a predefined sample or "cell" of blood and to capture the pulses reflected or "echoed" from the front and back surfaces of a blood sample.

A frequency-dependent sinusoidal waveform from a frequency generator is fed to a time intervalometer to create a predetermined artificial time delay between the reflected pulses. The frequency generator is adjusted to control the delay in such a way that the reflected pulses overlap, preferably by lining up the zero-crossing points of the waveforms corresponding to the two pulses as viewed on an oscilloscope connected to display the reflected acoustic energy pulses captured by the transducer. Under these conditions, the time interval between the two pulses correspond to and are calculated from the frequency of the frequency generator signal required to create the requisite time delay. Since the distance travelled by the pulses is a known factor based on the blood sample, i.e., the distance between the extreme reflecting surfaces of the sample, the acoustic velocity can be calculated by using Equation (2).

A major advantage in using the above-described glucose-monitoring technique according to the present invention is that, since acoustic energy pulses penetrate human skin and tissue with attenuation and dispersion coefficients which allow measurement path lengths of many centimeters, non-invasive monitoring of blood glucose concentration is possible as long as the measurements are made in parts of the human body where it is possible to accurately obtain reflections of acoustic energy from both the front and back surfaces of a well defined blood sample.

In making acoustic velocity measurements for determining glucose concentration in blood serum it is important to note that the measurement of acoustic velocity, as adjusted by the simultaneously monitored internal temperature of the blood, is effective as an indirect monitor of blood glucose concentration so long as that parameter is changing significantly more quickly than other physiological parameters and components, such as blood cells, proteins, cholesterol and triglycerides, which can also affect the acoustic velocity of the blood.

There are several applications under which this primary condition is satisfied. For instance, the physiological parameters, other than glucose, either remain suitably constant or may be predictably controlled during the time when the subject to be monitored is undergoing overnight rest. The acoustic measurement technique of this invention can therefore serve as an overnight monitor of incipient hypoglycemia in brittle diabetic individuals, particularly since frequent or even continuous measurement of blood acoustic velocity can be employed due to the noninvasive and painless modality of this measurement technique.

The acoustic measurement technique is particularly applicable as a monitor of glucose concentration levels in human subjects during periods in which the concentration levels could be changing quickly and where monitoring of such changes is important. Examples of such conditions are periods during childbirth for a diabetic individual, or during and after periods of significant physical stress or exercise.

It should also be noted that the measurement of acoustic velocity of blood does not serve as an absolute indicator of glucose concentration; this is because the measurement is sensitive to the effect of any and all components which change the density and adiabatic compressibility of the blood. Glucose is just one of several blood components which modify these parameters. However, as long as the glucose concentration in blood changes more rapidly than the other physiological parameters, as in the above-cited applications, the acoustic velocity measurement technique of this invention provides an accurate indication of the variation in glucose concentration levels, particularly when the dependence of these measurements on the internal blood temperature is accounted for.

Figure 1:
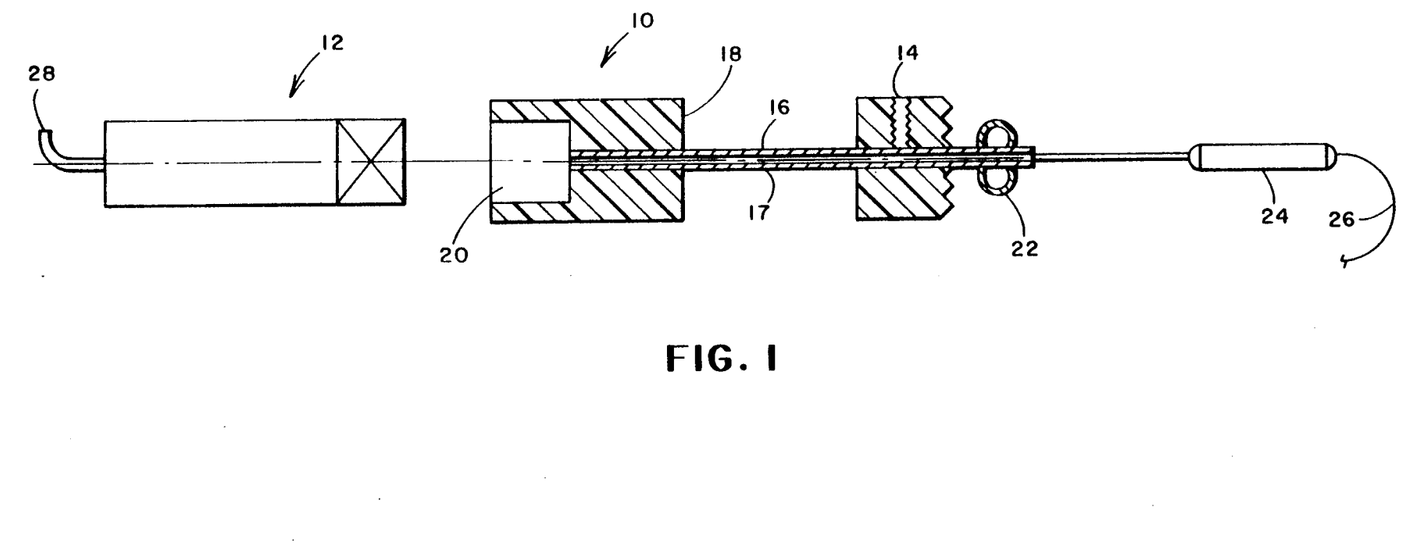
FIG. 1 is a schematic illustration of an earlobe-mounted glucose-monitoring probe assembly according to a preferred embodiment of this invention.

Referring now to FIG. 1, there is illustrated a preferred embodiment of apparatus adapted for using the acoustic velocity measurement technique of this invention for non-invasive monitoring of glucose concentration levels in individuals. The preferred embodiment of FIG. 1 is particularly adapted to perform the glucose concentration measurements through an earlobe of the individual. Performing the measurements about the earlobe offers several advantages. In particular, inaccuracy resulting from movement of the individual and, consequently, the variation in the known, fixed distance between the transducer and the reflecting surfaces, is avoided. This arrangement is also conducive to the convenient and simultaneous measurement of the internal temperature of the blood being sampled.

The glucose-monitoring probe 10 shown in FIG. 1 essentially comprises an acoustic transducer 12 for transmitting and receiving pulses of acoustic energy to and from a blood sample disposed between the transducer and a reflector 14 which is adapted to reflect back toward the transducer any acoustic energy incident thereupon. In the preferred embodiment, the probe 10 is particularly adapted for use with a pierced ear and includes a steel tubing 16 capable of extending through a pierced earlobe and serving as the main support means for the components of the probe.

The steel tubing is in the form of a cannula having an inner cavity 17, and is preferably formed of 23 gauge stainless steel tubing having an outer diameter of 0.025" and an inner diameter of 0.013". A buffer rod 18 formed of plexiglass (preferably $0.375\phi$) is mounted on one end of the cannula 16 and includes a flatbottomed hole 20 formed at the end remote from the cannula 16 which is adapted to accommodate the transducer 12 therein. The plexiglass rod 18 serves as a fixed delay means for achieving time separation of transmitted and reflected pulses. The transducer 12 is secured to the plexiglass rod 18 by means of a suitable adhesive (not shown), such as alkyl cyanoacrylate ester.

The reflector 14, which is preferably formed of plexiglass material (preferably 0.375φ) is adapted to be mounted on the cannula 16 in a manner permitting longitudinal displacement of the reflector along the axial length of the cannulae 16. A clip 22, which is akin to the clips commonly provided on earrings, is removably mounted on the cannula 16 and is capable of longitudinal displacement thereupon. The clip 22 is adapted to be positioned against the outer end of the reflector 14 so as to restrict subsequent longitudinal displacement of the reflector in the direction of the clip.

In use, the glucose-monitoring probe 10 is affixed to an ear of the individual to be monitored by first positioning the steel tubing or cannula 16 through a pierced earlobe so that the buffer rod 18 carrying the transducer 12 is positioned flush against the anterior section of the earlobe. Subsequently, the reflector 14 is placed over the tubing 16 and displaced longitudinally along the tubing until the reflector is positioned flush against the interior portion of the earlobe. At this point, the clip 22 is positioned on the tubing 16 and longitudinally displaced inwardly until it presses against the extreme end of the reflector 14. Since the clip 22 is adapted to be rigidly retained in its fixed position, the arrangement causes the probe to be mounted securely with the earlobe held between the buffer rod 18 and the reflector 14.

In order to monitor the internal temperature of the earlobe and, accordingly, the temperature of the blood sample contained therein, simultaneously with the acoustic measurements made by the transducer 12, a mini-hypodermic thermocouple 24 is disposed within the cannula 16. The output of thermocouple 24 becomes available on a signal wire 26 leading outwardly therefrom for use in adjusting the acoustic velocity calculation, as described above. In the preferred embodiment, the thermocouple 24 is selected to be a Type T Omega Model No. HYP-1-30-1/2T.

In the preferred embodiment, the transducer 12 is selected to be a KB-Aerotech Model OT-75AN, which is capable of generating a 7.5 MHz, 3.0 mmφ non-focused acoustic pulse as the probe signal. The acoustic energy pulses generated by the transducer 12 are first transmitted to the plexiglass buffer rod 18. Subsequently, the pulsed energy penetrates the tissue of the earlobe secured between the back surface of the buffer rod 18 and the front surface of the reflector 14 and traverses the blood serum contained therein.

The pulses transmitted from the transducer 12 are reflected from the interfaces of the blood sample at the buffer rod end and at the surface of the reflector 14 and received by the transducer 12. The transducer 12 converts these reflected energy pulses into corresponding electrical signals which become available at the signal line 28. The output signals generated by the transducer 12 are then analyzed in accordance with the "pulse echo overlap technique" described above in order to calculate the acoustic velocity, and, hence, the blood glucose concentration level in the individual.

Figure 2:
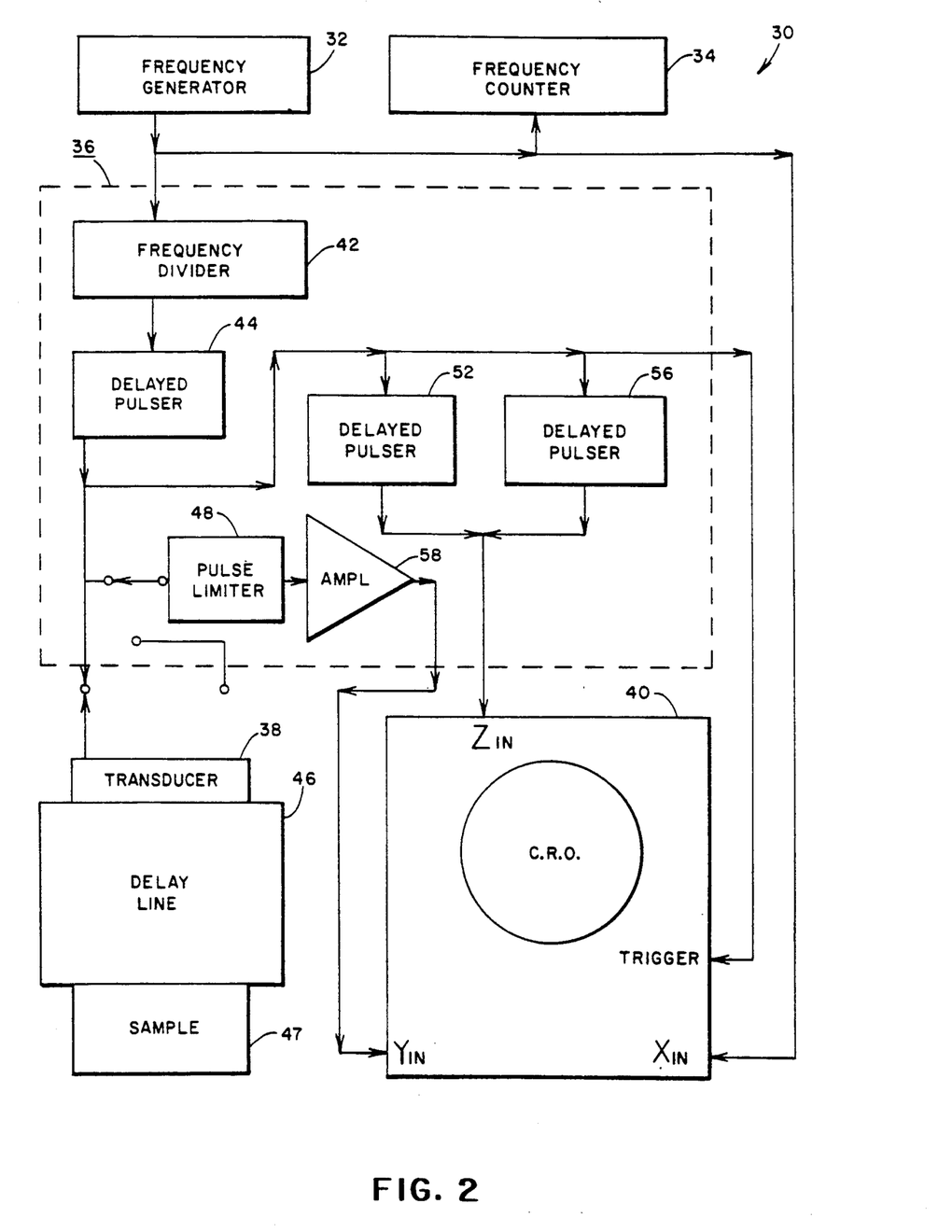
FIG. 2 is a schematic illustration of a preferred pulse echo monitoring system for making acoustic velocity measurements using the glucose-monitoring probe assembly illustrated in FIG. 1.

Referring now to FIG. 2, there is shown a block diagrammatic representation of a preferred system for analyzing acoustic energy pulses reflected from a blood sample after the pulses have been transduced to yield corresponding electrical signals, in order to ascertain the acoustic velocity of the blood. The monitoring system 30 essentially comprises a frequency generator 32 which is linked through a time intervalometer 36 to the output signals generated by the transducer 38. A standard cathode ray oscilloscope (CRO) 40 is used to display signals received from both the frequency generator 32 and from a commercially available time intervalometer 38. The acoustic velocity is determined by effecting the synchronous alignment of consecutive reflective echoes with the drive frequency of the frequency generator 32.

In a preferred embodiment, the measurement is made as follows. The frequency generator is set at a frequency "f" which is known to be close to the reciprocal of the transit time of an acoustic pulse through the sample. The reciprocal of the frequency "f", i.e., the time "t", must be approximately equal to the time between two echoes of interest, in particular two consecutive acoustic echoes. The frequency generator 32 is used to drive a frequency divider 42 included as a part of the time intervalometer 36. The frequency divider typically generates one synchronous pulse for every 100 or 1000 pulses of the frequency generator 32. This frequency division is necessary to ensure that the acoustic echoes which are measured by the transducer 38 have sufficient time to decay between consecutive trigger pulses.

Each synchronous trigger pulse from the frequency divider 42 is directed to a delayed pulser 44 which produces a high energy acoustic pulse which is no longer in phase with the pulse from the frequency generator 32. The pulse from the delayed pulser 44 is used for three essential functions. First, the delayed pulser 44 is connected, preferably through a coaxial cable, to the transducer 38 and the delayed pulse is used to energize the transducer. A delay line 46 separates the transducer 38 and the sample 47, thereby ensuring a fixed time delay between the transmitted and reflected pulses. According to the preferred embodiment of FIG. 1, the plexiglass rod 20 functions as the delay line 46. The delayed pulse from the pulser 44 is also used to trigger the X-axis sweep of the CRO. In addition, the pulse is used to trigger two delayed pulsers 52 and 56 which are used to intensify the Y-axis CRO trace.

Consecutive echoes of the acoustic impulse delivered to the sample are displayed in real time on the Y-axis of the CRO by directing the reflected signals sensed by the transducer through a pulse limiter 48 and an amplifier 50 to the CRO. The function of the pulse limiter is to ensure that the high intensity signals produced by the delayed pulser 44 which are reflected through the sample do not overload the amplifier circuits of the CRO. The delayed pulsers 52 and 56 are used to intensify the two acoustic echoes of interest, thus rejecting spurious internal reflection.

After the two echoes have been positioned on the screen, the main intensity of the CRO is turned down to such a level that only the two intensified echoes are visible. The approximate difference in travel time between the two intensified echoes can now be calculated from the CRO sweep calibration. The frequency generator 32 is then set at a frequency corresponding to the reciprocal of the calculated time period. This new calculated frequency is a better estimate of the reciprocal time than the originally selected frequency setting of the frequency generator 32.

Subsequently, the X-axis selector switch of the CRO is changed so that instead of being driven by the frequency divider 42, it is driven directly by the sinusoidal pulses of the frequency generator 32. Accordingly, the two echoes of interest will be in close coincidence on the CRO. They can then be brought into perfect coincidence by a fine adjustment of the frequency "f" from the frequency generator 32 so that the zero-crossing points on each of the displayed waveforms are effectively lined up.

In the system of FIG. 2, a standard frequency counter 34 is linked to the frequency generator 32 and serves as a verification of the instantaneous frequency generated thereby. The frequency generator 32 is a commercially available instrument and may either be a continuous wave (CW) oscillator or a pulse oscillator. Although the frequency generator 32 is shown in FIG. 2 as being independent of the time intervalometer 36, the generator 32 and the associated frequency counter 34 may actually form part of and be totally contained within the intervalometer unit itself.

When the two waveforms so overlap, the time delay between the pulses corresponds inversely to the output frequency of the generator 32. Since the distance between the two reflecting surfaces of the blood sample is a known factor, the acoustic velocity of the blood sample can be calculated at this point by using the relationship defined by Equation (2).

The applicants have determined by way of ultrasonic studies focusing on the relationship between acoustic velocity and glucose concentration in a serum that the acoustic velocity bears a linear relationship to glucose concentration. Accordingly, a series of acoustic velocity measurements of the above type can be made at specific time intervals and, because of the demonstrated linear relationship between acoustic velocity and glucose concentration, these measurements serve as an indication of the glucose concentration levels at those points in time. Each of these acoustic velocity measurements can also be compensated for temperature effects by instantaneously measuring the internal temperature of the blood sample and using the relationship defined by Equation (3).

Figure 3:
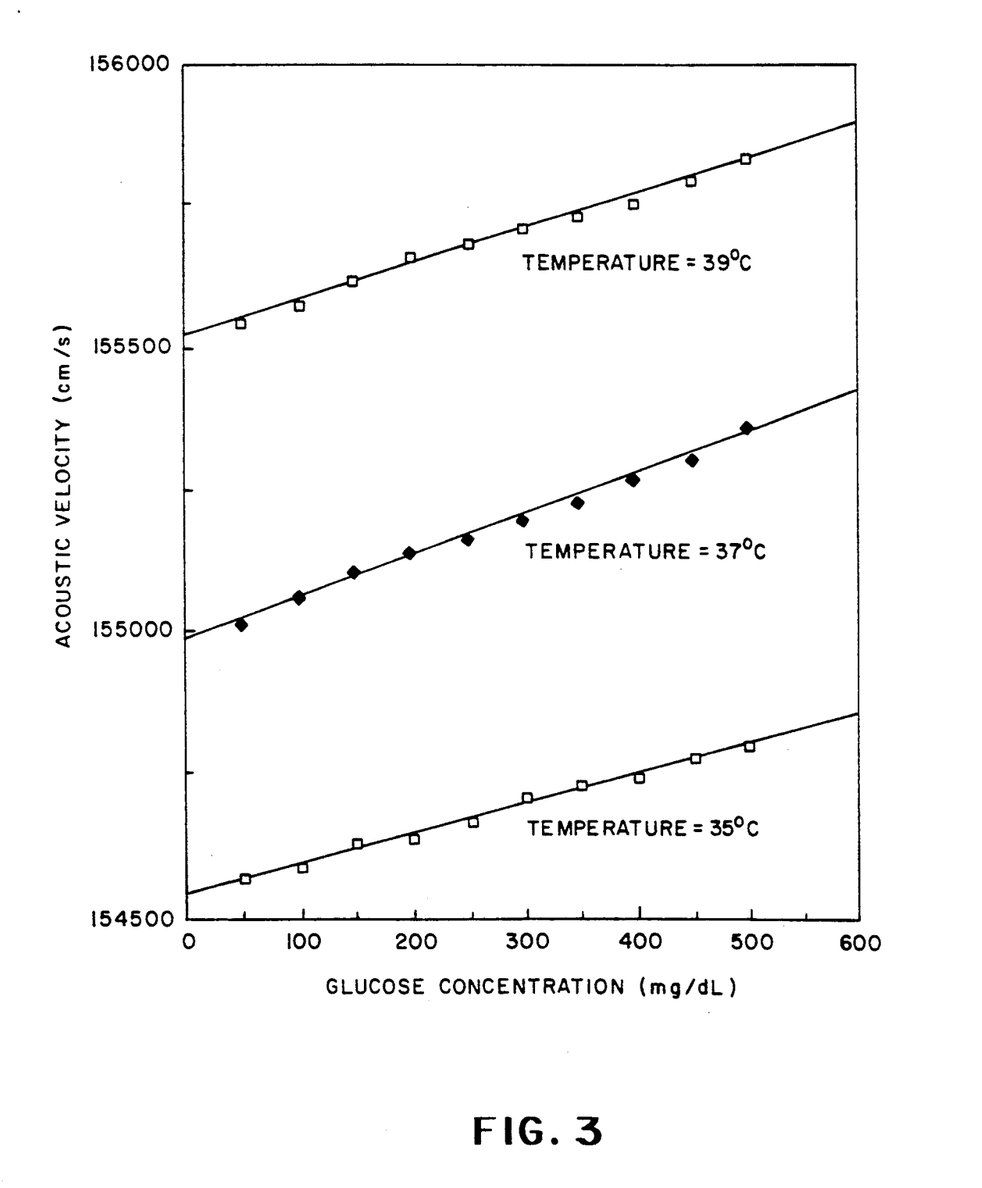
FIG. 3 is a graphical illustration of the linear relation between glucose concentration level and acoustic velocity in a glucose solution.

Referring now to FIG. 3, there is shown a graphical illustration of the applicants' experimental demonstration of the linear relationship between glucose concentration levels in a glucose solution and corresponding acoustic velocity of the solution. As shown therein, the acoustic velocity of the solution increases linearly with increasing glucose concentration. Although the degree of linearity in this relationship remains substantially the same with changes in temperature, the three graphs shown in FIG. 3 illustrate that increases in the internal temperature of the glucose solution directly increase the threshold acoustic velocity of the solution.

Figure 4:
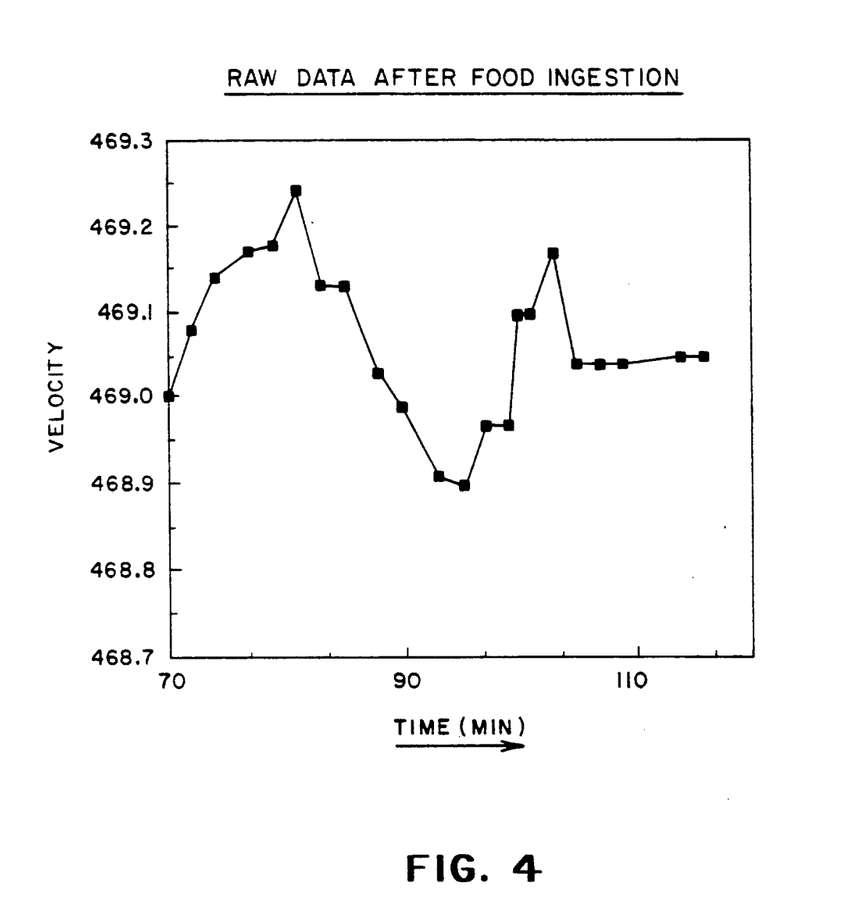
FIG. 4 is a graphical representation of experimental measurements of acoustic velocity/glucose concentration made by using the glucose-monitoring probe assembly of FIG. 1.

Experimental results using the glucose monitoring technique of this invention and using a glucose monitor in accordance with the preferred embodiment of FIG. 1 have been extremely successful. Representative results are illustrated in FIG. 4 which is a graphical illustration of the variation in acoustic velocity with respect to time for an individual using the ear-mounted glucose monitor of FIG. 1. For purposes of the experiment, the individual was maintained under normal rest conditions for a two hour period and the acoustic velocity of blood continuously measured through the individual's earlobe over that period. After 60 minutes, the subject was given a glucose-rich diet. FIG. 4 is a representation of the velocity changes detected by the monitor in the 70-120 minute time period relative to the start of the experiment.

Prior to ingestion of the food, no significant change in acoustic velocity was picked up by the monitor. As seen in FIG. 4, ten (10) minutes after ingestion of the glucose-rich diet, significant acoustic velocity changes were picked up by the monitor. The measured changes in acoustic velocity closely track the expected changes in blood glucose concentration as seen by the sharp rise in acoustic velocity after the glucose ingestion and then the subsequent fall in velocity corresponding to the decline in blood glucose level in the following time period.

It will be understood that the earlobe-mounted probe assembly according to the preferred embodiment of FIG. 1 is an illustrative example of one assembly that can be used to accomplish the purpose of the present invention. The principles described herein can be used effectively for making alternative arrangements for monitoring the glucose concentration levels in an individual's blood. For instance, the probe assembly could be designed so that the acoustic transducer and the reflector attach to the web of skin between the thumb and forefinger of a subject's hand, along with appropriate means for strapping the assembly in place to minimize any movement thereof.

We claim:

1. A non-invasive monitor of changes in blood glucose concentration in a tissue specimen comprising:
   means for transmitting and receiving ultrasonic energy pulses to and from the tissue specimen;
   means for reflecting said ultrasonic energy pulses from said tissue specimen, said reflecting means being spaced from said transmitting and receiving means,
   means for measuring the travel time between selected ones of said reflected ultrasonic energy pulses to calculate the associated acoustic velocity; and
   support means for interconnecting and mounting said transmitting and receiving means for placement of the tissue specimen therebetween, whereby the calculated acoustic velocity is representative of the blood glucose concentration in said tissue specimen.

2. The non-invasive monitor set forth in claim 1 further comprising a thermocouple mounted on said support means for monitoring the internal temperature of said tissue specimen.

3. The non-invasive monitor of claim 2 wherein said monitored temperature is used to adjust said calculated acoustic velocity.

4. Apparatus for non-invasive monitoring of blood glucose concentration levels in a blood sample, comprising:
   means disposed in proximity to one of two opposing surfaces of the blood sample for transmitting and receiving a series of acoustic energy pulses to and from said blood sample;
   means disposed adjacent the other of said two opposing surfaces of said sample for reflecting said acoustic energy pulses after having passed through said blood sample;
   means for measuring the travel time between selected ones of said reflected ultrasonic energy pulses to calculate the associated acoustic velocity, said acoustic velocity being representative of the blood glucose concentration;
   support means for interconnecting and mounting said transmitting and receiving means and said reflecting means for placement of said blood sample therebetween; and
   means disposed on said support means for monitoring the temperature of said blood sample.

5. The non-invasive blood glucose concentration monitor claimed in claim 4 wherein said monitored temperature is used to adjust said calculated acoustic velocity.

6. A method for non-invasive monitoring of changes in blood glucose concentration in a tissue specimen, comprising the steps of:
   generating pulses of acoustic energy;
   transmitting said pulses of acoustic energy into the tissue specimen;
   sensing the pulses of acoustic energy reflected back from said tissue specimen;
   measuring the travel time between selected ones of said reflected acoustic energy pulses; and
   using said measurements of travel time to calculate the acoustic velocity in said specimen, whereby said calculated acoustic velocity provides an indication of the blood glucose concentration in said tissue specimen.

7. The method for non-invasive monitoring of blood glucose concentration set forth in claim 6 further comprising the steps of monitoring the internal temperature of said tissue specimen and using the monitored temperature to adjust said calculated acoustic velocity.

8. A method of non-invasive monitoring of qlucose concentration levels in blood or like glucose-containing solution, said method comprising the steps of:
   transmitting acoustic energy pulses into said solution;
   receiving acoustic energy pulses reflected back from said solution; and
   analyzing said reflected pulses to determine the acoustic velocity of said solution, whereby said determined acoustic velocity provides an indication of the glucose concentration level of said solution.

9. The non-invasive glucose monitoring method of claim 8 wherein an acoustic transducer is used for transmitting and receiving said acoustic energy pulses to and from said solution.

10. The non-invasive glucose monitoring method of claim 8 wherein reflective means are provided adjacent said solution to facilitate reflection of said acoustic energy pulses.

11. The non-invasive glucose monitoring method of claim 8 wherein the travel time between selected ones of said reflected pulses is determined and the acoustic velocity of said solution calculated therefrom.

12. The non-invasive monitoring technique of claim 8 further including the steps of monitoring the internal temperature of said solution and using the monitored temperature to adjust said determined acoustic velocity.

13. A method of non-invasive monitoring of glucose concentration levels in blood or other glucose-containing solution by
   (i) measuring the acoustic velocity of said solution; and
   (ii) using the measured acoustic velocity as a linear measure of the glucose concentration level in said solution.

14. The non-invasive glucose monitoring method of claim 13 wherein the acoustic velocity is measured by using an acoustic transducer for transmitting and receiving acoustic energy pulses to and from said solution and determining the travel time between selected ones of reflected pulses received from said solution.

15. The non-invasive glucose monitoring method of claim 14 wherein said acoustic transducer is used in conjunction with associated delay means for delaying, by a fixed time period, reflected pulses received by said transducer from said solution.

* * * * *